United States Patent [19]

Matsunaga et al.

[11] Patent Number: 5,043,424

[45] Date of Patent: Aug. 27, 1991

[54] MODIFICATION METHOD FOR PEPTIDES AND PROTEINS BY REACTING WITH A PHOSPHORIC ACID ESTER

[75] Inventors: Akira Matsunaga; Nobutaka Horinishi, both of Wakayama; Junya Wakatsuki, Utsunomiya; Takashi Imamura, Wakayama; Tomihiro Kurosaki, Osaka, all of Japan

[73] Assignee: Kao Corporation, Tokyo, Japan

[21] Appl. No.: 260,709

[22] Filed: Oct. 21, 1988

[30] Foreign Application Priority Data

Oct. 21, 1987 [JP] Japan .................. 62-265990

[51] Int. Cl.⁵ .................. C07K 3/08; C07K 17/06
[52] U.S. Cl. .................. 530/345; 435/177; 435/188; 435/198; 530/363; 530/408; 530/409; 530/410; 562/575
[58] Field of Search .......... 530/408, 409, 410, 363, 530/345; 425/177, 188, 198; 562/575

[56] References Cited

U.S. PATENT DOCUMENTS 2,768,997 10/1956 Reeves et al. .................. 530/363

*Primary Examiner*—Howard E. Schain
*Attorney, Agent, or Firm*—Oblon, Spivak, McClelland, Maier & Neustadt

[57] ABSTRACT

A peptide or protein is modified by reacting a phosphoric acid ester represented by the following general formula (I) with a peptide or protein:

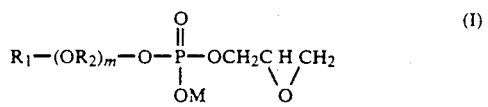

wherein $R_1$ means a linear or branched, $C_{1-36}$ alkyl or $C_{2-36}$ alkenyl group whose hydrogen atom or atoms may be substituted by the corresponding number of fluorine atom(s) or a phenyl group substituted by at least one linear or branched $C_{1-15}$ alkyl group, $R_2$ denotes a $C_{2-3}$ alkylene group, m stands for a number of 0–30, and M is a hydrogen atom, an alkali metal ion, an alkaline earth metal ion, an ammonium ion, an alkylamine residue or an alkanolamine residue.

16 Claims, No Drawings

MODIFICATION METHOD FOR PEPTIDES AND PROTEINS BY REACTING WITH A PHOSPHORIC ACID ESTER

BACKGROUND OF THE INVENTION

1) Field of the Invention

This invention relates to a method for the modification of a peptide or protein, and more specifically to a method for the modification of a peptide or protein by causing a specific phosphoric acid to act on the peptide or protein.

2) Description of the Related Art

Among peptides and proteins led by enzymes, there are many substances which are used or expected to be used as pharmaceutical agents such as therapeutic agents and diagnostics, reaction reagents or industrial reactors owing to their inherent function. These substances, especially, enzyme proteins are however accompanied by a drawback that the ranges of their utility are limited for their instable properties, dissolution characteristics, etc. With a view toward using proteins which are existent in the nature, a great deal of work has been carried out in recent years so as to develop modified proteins while retaining characteristics which naturally-existent proteins have, typified by modified enzymes imparted with some additional useful characteristics.

Developed as such modified proteins include, for example, proteins modified with polyethylene glycol and proteins with a functional high-molecular compound coupled thereto by using a crosslinking agent such as dicyclohexylcarbodiimide. However, the former modified proteins require purification of conjugates of polyethylene glycol as a modifier and proteins, e.g., cyanuric chloride by chromatography or the like, and involve a problem that the procedure is too irksome to conduct the production on a large scale. The latter modified proteins involve a problem of intracrosslinking of the protein or high molecular compound itself.

SUMMARY OF THE INVENTION

The present inventors have carried out an extensive investigation under such circumstances. As a result, it has been found that the reaction of a phosphoric acid ester represented by the general formula (I), which is obtained with a high purity and in a high yield by a simple operation, with a peptide or protein enables easy introduction of the corresponding phosphoric acid ester group in the peptide or protein and physicochemical properties of the peptide or protein can be modified by the introduction of the phosphoric acid ester group, leading to completion of this invention.

In one aspect of this invention, there is thus provided a method for the modification of a peptide or protein, which comprises reacting a phosphoric acid ester represented by the following general formula (I) with a peptide or protein:

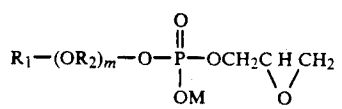
(I)

wherein $R_1$ means a linear or branched, $C_{1-36}$ alkyl or $C_{2-36}$ alkenyl group whose hydrogen atom or atoms may be substituted by the corresponding number of fluorine atom(s) or a phenyl group substituted by at least one linear or branched $C_{1-15}$ alkyl group, $R_2$ denotes a $C_{2-3}$ alkylene group, m stands for a number of 0–30, and M is a hydrogen atom, an alkali metal ion, an alkaline earth metal ion, an ammonium ion, an alkylamine residue or an alkanolamine residue.

The phosphoric acid ester (I) permits introduction of one or more phosphoric acid ester groups in a peptide or protein by a simple operation. Moreover, physicochemical properties of the peptide or protein, such as solubility and surface charge, can be modified by the introduction of such phosphoric acid ester group or groups. In addition, the modification method of this invention is useful as an industrial modification method for peptides and proteins since the phosphoric acid ester (I) required in the practice of this invention can be prepared with ease industrially.

The above and other objects, features and advantages of the present invention will become apparent from the following description and the appended claim.

DETAILED DESCRIPTION OF THE INVENTION AND PREFERRED EMBODIMENTS

The phosphoric acid ester of the general formula (I) useful in the practice of this invention may be obtained by any process. For example, it can be produced easily on an industrial scale as proposed by some of the present inventors, namely, by reacting an epihalohydrin with a high-purity monoalkali metal salt of a phosphoric acid ester and then conducting ring-closing of the reaction product with an alkali.

Namely, the phosphoric acid ester can be produced with ease industrially by reacting an epihalohydrin represented by the formula (III) with a monoalkali metal salt of a phosphoric acid monoester, which is represented by the formula (II), and then conducting ring-closing of the reaction product with an alkali.

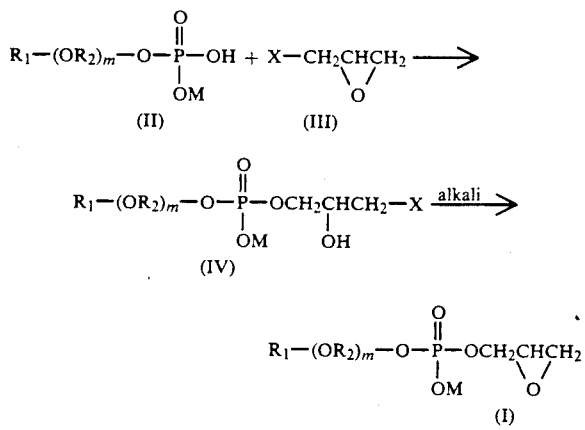

wherein X is a halogen atom and $R_1$, $R_2$, M and m have the same meanings as described above.

Illustrative examples of the linear or branched, $C_{1-36}$ alkyl or $C_{2-36}$ alkenyl group whose hydrogen atom or atoms may be substituted by the corresponding number of fluorine atom(s) or a phenyl group substituted by at least one linear or branched $C_{1-15}$ alkyl group, which is represented by $R_1$ in the phosphoric acid ester of the formula (I) useful in the practice of this invention, may include methyl, ethyl, butyl, hexyl, octyl, decyl, dodecyl, tetradecyl, hexadecyl, octadecyl, docosyl, tetracosyl, triacontyl, 2-ethylhexyl, 2-octyldodecyl, 2-dodecylhexadecyl, 2-tetradecyloctadecyl, monomethyl-branched-isostearyl, tridecafluorooctyl, heptadecafluorododecyl, heneicosafluorododecyl, pentacosafluorotetradecyl, nonacosafluorohexadecyl, tritriacontafluorooctadecyl, 2-pentafluoroethylpentafluorohexyl, 2-tridecafluorohexyltridecafluorodecyl, 2-heptadecafluorooctylheptadecafluorododecyl, 2-heneicosafluorodecylheneicosafluorotetradecyl, 2-pentacosafluorododecylpentacosafluorohexadecyl, 2-nonacosafluorotetradecylnonacosafluorooctadecyl, octenyl, decenyl, dodecenyl, tetradecenyl, hexadecenyl, octadecenyl, dococenyl, tetracocenyl, triacontenyl, ethylphenyl, butylphenyl, hexylphenyl, octylphenyl, nonylphenyl, and the like. Among these, those having 8–36 carbon atoms, especially, 8–24 carbon atoms are preferred. As exemplary $C_{2-3}$ alkylene groups represented by $R_2$, may be mentioned ethylene, 1-methylethylene, propylene and the like.

Peptides and proteins, which may be modified with the phosphoric acid ester represented by the formula (I) in accordance with this invention, include peptides and proteins which are composed of two or more amino acids and are available naturally or by artificial synthesis, and their derivatives and salts. No further limitation is imposed thereon. As exemplary peptides and proteins, may be mentioned collagen, gelatin, keratin, albumin, globulin, fibrinogen, actin, elastin, phospholipase, lipase, phosphorylase, trypsin, soybean protein, wheat protein, fish protein, glucagon, glycylglycine, glycylalanine, glycylleucine, alanylalanine, glutathione, methionylleucylphenylalanine, alanylglycylcerylglutamine, leucylenkephalin, and salts thereof.

The phosphoric acid ester represented by the formula (I) include salts. In the practice of this invention, the phosphoric acid ester represented by the formula (I) may be used after its isolation or in the form of a reaction mixture which is obtained by reacting the phosphoric acid ester represented by the formula (IV) with an alkali. This invention may also be practised by adding the phosphoric acid ester represented by the formula (IV) to the peptide or protein and then causing an alkali to act on the reaction mixture.

In the present invention, the molar ratio of the phosphoric acid ester represented by the formula (I) to the peptide or protein to be reacted each other varies depending on properties required. Although no particular limitation is hence imposed thereon, they are generally used at a ratio in a range of from 0.01:1 to 100:1. As a solvent for the reaction, an inert polar solvent is preferred. Water, methyl alcohol, ethyl alcohol, 2-propanol and the like may be mentioned by way of example. They may be used either singly or in combination. It is preferable to add a suitable amount of a salt to the reaction system so as to avoid denaturation of the peptide or protein.

The reaction temperature may range from 0° C. to 100° C. It is however preferable to conduct the reaction, especially, at 30°–90° C. in order to avoid denaturation of the resultant product.

Although it is not fully clear on which site or sites of the peptide or protein the phosphoric acid ester represented by the formula (I) acts upon modification of the peptide or protein with the phosphoric acid ester in this invention, amino, mercapto, hydroxyl and carboxyl groups may be mentioned by way of example as sites to be reacted. The phosphoric acid ester is believed to react to amino group or mercapto group or their groups in particular. It should however be borne in mind that no particular limitation is imposed on the site or sites of the peptide or protein to which the phosphoric acid ester represented by the general formula (I) reacts when the peptide or protein is modified with the phosphoric acid ester.

This invention will hereinafter be described by the following Examples.

REFERENCE EXAMPLE 1: Preparation of sodium dodecylglycidylphosphate

A reactor was charged with 50.0 g (0.131 mole) of sodium dodecyl 2-hydroxy-3-chloropropylphosphate, followed by an addition of 1000 ml of ethanol. The contents were stirred and heated to 70° C. so that a homogeneous mixture was formed. After cooling the reaction system to room temperature, a solution of 5.25 g (0.131 mole) of sodium hydroxide in 100 ml of ethanol was added gradually, followed by stirring at the same temperature for 3 hours. The reaction mixture was analyzed by HPLC (high-performance liquid chromatography; the same definition will hereinafter apply equally). Upon observation of disappearance of peaks corresponding to the raw materials and appearance of a new peak corresponding to the reaction product, the reaction was terminated. Subsequent to removal of precipitated sodium chloride by filtration, ethanol was distilled off under reduced pressure to obtain 45.0 g of sodium dodecyl glycidylphosphate (yield: 99.5%).

Elemental analysis: Calculated: C, 52.32; H, 8.78; P, 9.0; Na, 6.7. Found: C, 52.10; H, 8.71; P, 8.8; Na, 6.5.

EXAMPLE 1

A reactor was charged with 10 g (0.0757 mole) of glycylglycine, followed by an addition of 100 ml of water. The contents were stirred and heated to 70° C. so that a homogeneous mixture was formed. While maintaining the above temperature, a solution of 28.8 g (0.0757 mole) of sodium dodecyl glycidylphosphate obtained in Referential Example 1 in 1000 ml of ethanol was added dropwise, followed by stirring for 6 hours. The reaction mixture was analyzed by HPLC. Upon observation of disappearance of peaks corresponding to the raw materials and appearance of a new peak corresponding to the reaction product, the reaction was terminated. Subsequent to the termination of the reaction, the solvents were distilled off under reduced pressure to obtain 38.5 g of the following compound (yield: 99.2%).

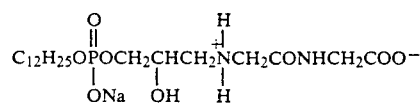

Elemental analysis: Calculated: C, 47.89; H, 8.04; P, 6.5; N, 5.88; Na, 4.8. Found: C, 47.70; H, 8.00; P, 6.4; N, 5.80; Na, 4.7.

EXAMPLE 2

A reactor was charged with 10 g (0.0531 mole) of glycylleucine, followed by an addition of 100 ml of water. The contents were stirred and heated to 70° C. so that a homogeneous mixture was formed. While maintaining the above temperature, a solution of 12.7 g (0.0266 mole) of sodium trioxyethylenedodecylether glycidylphosphate obtained in a similar manner as in Referential Example 1 in 1000 ml of ethanol was added dropwise, followed by stirring for 6 hours. The reaction mixture was analyzed by HPLC. Upon observation of disappearance of peaks corresponding to the raw materials and appearance of a new peak corresponding to the reaction product, the reaction was terminated. Subsequent to the termination of the reaction, the reaction product as fractionated by HPLC and the solvents were distilled off under reduced pressure to obtain 17.5 g of the following compound (yield: 99.1%).

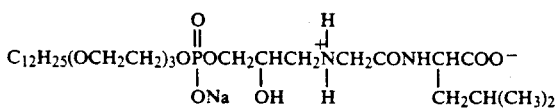

Elemental analysis: Calculated: C, 52.40; H, 8.79; P, 4.7; N, 4.21; Na, 3.5. Found: C, 52.10; H, 8.65; P, 4.5; N, 4.17; Na, 3.3.

EXAMPLE 3

A reactor was charged with 1.00 g (0.00624 mole) of alanylalanine, followed by an addition of 62.4 ml of 0.1N aqueous solution of sodium hydroxide. The contents were stirred and heated to 70° C. so that a homogeneous mixture was formed. While maintaining the above temperature, a solution of 4.11 g (0.00624 mole) of sodium heptadecafluorodecyl glycidylphosphate obtained in a similar manner as in Referential Example 1 in 100 ml of ethanol was added dropwise, followed by stirring for 6 hours. The reaction mixture was analyzed by HPLC. Upon observation of disappearance of peaks corresponding to the raw materials and appearance of a new peak corresponding to the reaction product, the reaction was terminated. Subsequent to the termination of the reaction, 62.4 ml of 0.1N hydrochloric acid was added to neutralize the reaction mixture. After desalting the resultant mixture by dialysis, the solvents were distilled off under reduced pressure to obtain 4.75 g of the following compound (yield: 97.3%).

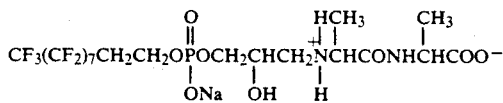

Elemental analysis: Calculated: C, 29.17; H, 2.71; F, 41; P, 4.0; N, 3.58; Na, 2.9. Found: C, 29.08; H, 2.65; F, 40; P, 3.8; N, 3.46; Na, 2.7.

EXAMPLE 4

A reactor was charged with 1 g (0.00684 mole) of glycylalanine, followed by an addition of 10 ml of water. The contents were stirred and heated to 70° C. so that a homogeneous mixture was formed. While maintaining the above temperature, 20 g (0.00684 mole) of an ethanol solution of sodium butyl glycidylphosphate, said ethanol solution having been obtained by reacting 1.84 g (0.00684 mole) of sodium butyl 2-hydroxy-3-chloropropylphosphate with sodium hydroxide in ethanol as a solvent, was added dropwise, followed by stirring for 6 hours. The reaction mixture was analyzed by HPLC. Upon observation of disappearance of peaks corresponding to the raw materials and appearance of a new peak, the reaction was terminated. Subsequent to the termination of the reaction, the reaction mixture was desalted by dialysis and the solvents were distilled off under reduced pressure to obtain 2.52 g of the following compound (yield: 97.4%).

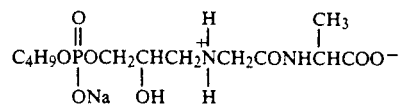

Elemental analysis: Calculated: C, 38.10; H, 6.39; P, 8.2; N, 7.41; Na, 6.1. Found: C, 37.80; H, 6.34; P, 8.1; N, 7.37; Na, 5.9.

EXAMPLE 5

A reactor was charged with 0.1 g of BSA (bovine serum albumin), followed by an addition of 5 ml of a 0.2M phosphate buffer (pH 9.5). The contents were shaken and heated to 40° C. so that a homogenous mixture was formed. While maintaining the above temperature, a solution of 0.400 g (0.00100 mole) of sodium 2-hexyldecyl glycidylphosphate obtained in a similar manner as in Referential Example 1 in 4 ml of ethanol was added dropwise, followed by shaking for 12 hours. Analysis of the thus-obtained reaction mixture by SDS-polyacrylamide eletrophoresis indicated an increase in the molecular weight. It was hence confirmed that the phosphoric acid ester had modified BSA.

EXAMPLE 6

Swine-spleen-derived phospholipase $A_2$ was dissolved at 10 mg/ml in a 0.2M phosphate buffer (pH 9.5). Added to 100 μl of the enzyme solution was 25 μl of a solution of 0.946 g (0.00250 mole) of sodium nonylphenyl glycidylphosphate obtained in a similar manner as in Referential Example 1 in 10 ml of ethanol, followed by heating to 50° C. Shaking was continued for 12 hours while maintaining the above temperature. After completion of the reaction, the target product was purified by gel filtration and was then analyzed by $^{31}$P-NMR. A spectrum derived from a phosphorus compound was detected, thereby confirming the modification of phospholipase $A_2$ with the phosphoric acid ester.

What is claimed is:

1. A method for the modification of a peptide or protein, which comprises the steps of:

reacting a phosphoric acid ester represented by the following formula (I) with a peptide or protein:

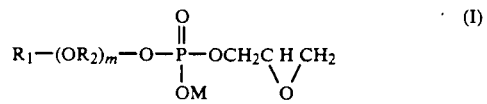

wherein $R_1$ is a linear or branched, $C_{1-36}$ alkyl or $C_{2-36}$ alkenyl group whose hydrogen atom or atoms may be substituted by the corresponding number of fluorine atom(s) or a phenyl group substituted by at least one linear or branched $C_{1-15}$ alkyl group, $R_2$ is a $C_{2-3}$ alkylene group, m is 0–30, and M is a hydrogen atom, an alkali metal ion, an alkaline earth metal ion, an ammonium ion, an alkylamine residue or an alkanolamine residue, thereby introducing the group represented by formula (II) into said peptide or protein

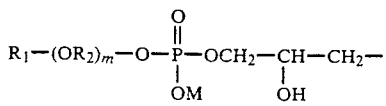

(II)

wherein $R_1$, $R_2$, m and M have the same meanings as above.

2. The method of claim 1, wherein said peptide or protein comprises two or more amino acids.

3. The method of claim 1, wherein $R_1$ contains 8-36 carbon atoms.

4. The method of claim 1, wherein $R_1$ contains 8-24 carbon atoms.

5. The method of claim 1, wherein the molar ratio of said phosphoric acid ester and said peptide or protein is in the range from 0.01:1 to 100:1.

6. The method of claim 1, wherein said reacting step is conducted in a solvent.

7. The method of claim 6, wherein said solvent is an inert polar solvent.

8. The method of claim 1, wherein said reacting step is conducted at a temperature in the range 0°-100° C.

9. The method of claim 8, wherein said temperature is in the range 30°-90° C.

10. The method of claim 1, wherein said phosphoric acid ester is bonded to an amino, mercapto, hydroxyl or carboxyl group on said peptide or protein.

11. The method of claim 1, wherein said phosphoric acid ester is prepared by reacting a compound having formula (IV)

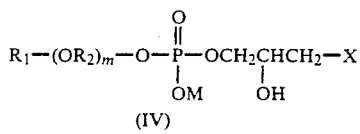

(IV)

with an alkali, wherein X is a halogen atom.

12. The method of claim 11, wherein said peptide or protein is added to the reaction produce of said compound having formula (IV) and said alkali.

13. The method of claim 1, wherein said reacting step comprises mixing said phosphoric acid ester and said peptide or protein and then adding an alkali to said mixture.

14. A modified peptide or protein prepared by the method of claim 1.

15. A modified peptide or protein prepared by the method of claim 12.

16. A modified protein or peptide prepared by the method of claim 13.

* * * * *

UNITED STATES PATENT AND TRADEMARK OFFICE
CERTIFICATE OF CORRECTION

PATENT NO. : 5,043,424
DATED : AUGUST 27, 1991
INVENTOR(S) : AKIRA MATSUNAGA ET AL

It is certified that error appears in the above-identified patent and that said Letters Patent is hereby corrected as shown below:

Column 1, line 32, delete "crosslinking", insert
--cross-linking--;
lines 39 and 40, delete "intracrosslinking", insert
--intracross-linking--;
line 40, delete "high molecular", insert
--high-molecular--.

Column 8, Claim 12, line 16, delete "produce", insert
--product--.

Signed and Sealed this

Tenth Day of August, 1993

Attest:

MICHAEL K. KIRK

Attesting Officer

Acting Commissioner of Patents and Trademarks